United States Patent [19]

Meltzer et al.

[11] 4,285,906

[45] Aug. 25, 1981

[54] ROTATABLE DETECTOR

[75] Inventors: Robert J. Meltzer, Long Valley; Donald H. Hansen, Convent Station, both of N.J.

[73] Assignee: Warner-Lambert Company, Morris Plains, N.J.

[21] Appl. No.: 38,040

[22] Filed: May 11, 1979

[51] Int. Cl.³ .................... G01N 21/82; G01N 21/27; G01N 21/03; G01N 33/86
[52] U.S. Cl. ........................................ 422/64; 422/73; 250/432 R; 356/435
[58] Field of Search ............... 422/64, 67, 73; 356/39, 356/246, 435; 250/208, 432 R; 364/497, 498

[56] References Cited

U.S. PATENT DOCUMENTS

| 3,477,822 | 11/1969 | Hamilton | 422/61 |
| 3,540,858 | 11/1970 | Rochte et al. | 422/67 |
| 3,969,079 | 7/1976 | Catarious et al. | 23/230 B |
| 4,234,538 | 11/1980 | Ginsberg et al. | 422/67 X |

FOREIGN PATENT DOCUMENTS 2635582 3/1977 Fed. Rep. of Germany .
1192008 5/1970 United Kingdom .

OTHER PUBLICATIONS

Anderson, Analytical Biochemistry, 28, 545–562, (1969).

Primary Examiner—Ronald Serwin
Attorney, Agent, or Firm—Alan H. Spencer

[57] ABSTRACT

A rotatable detector for continuously monitoring twelve blood samples being evaluated by an instrument is disclosed. Each sample is held in a separate cuvette forming part of a cuvette tray. A single bulb illuminates all twelve cuvettes and the light passing through each cuvette is carried to a separate detector for that cuvette by a respective one of twelve light pipes. The cuvette tray receptacle bulb and twelve detectors all rotate as a unit to permit reagent dispensing at a single station while continuously monitoring the light transmission of each sample.

3 Claims, 3 Drawing Figures

ROTATABLE DETECTOR

BACKGROUND OF THE INVENTION

Automated coagualtion testing has been accomplished by apparatus developed in recent years. Thus, apparatus has been devloped for testing plasma samples for prothrombin time, activated partial thromboplastin time, factor assays, and many other tests. Prior art devices have included means for pre-warming components in fluids and have utilized photoelectric systems for measuring coagulation time. In fact, such devices as the COAG-A-MATE single channel clot detection system sold by General Diagnostics Division of the Warner-Lambert Company has been very effective for such measurements. Devices for a similar purpose are manufactured by Medical Laboratory Automation, Inc. as the MLA Electra 620 and 600 Coagulation Timers. These devices have been described in U.S. Pat. Nos. 3,477,822 and 3,540,858. Additionally, many trays have been developed for testing samples photo-optically, which prior art devices are shown in U.S. Pat. Nos. 2,879,141; 3,038,340; 3,041,146; 3,368,872; 3,449,959; 3,469,438; 3,477,821; 3,477,822; 3,480,398; 3,480,399; 3,532,470; 3,540,858; 3,554,704; 3,544,705; 3,574,553; 3,594,129; 3,676,080; 3,690,833; 3,692,487; 3,692,488; 3,704,099; and 3,707,354.

U.S. Pat. No. 3,969,079 relates to an improved photo-optical clot detection apparatus having dual channels to provide simultaneous evaluation of two samples. The circular cuvette remains stationary during the test. Reagent dispensing means is provided at both sample stations.

SUMMARY OF THE INVENTION

The present invention is directed to a multi channel photo-optical clot detection system for the automatic determination of prothrombin times and activated partial thromboplastin times and other related coagulation tests. Whereas in the past, only single and dual channel operation could be effected, the present invention is directed to a multi channel operation which can be effected within nearly the same time period as prior art systems. In such a system, as many as twelve plasma samples can be tested in about the same period of time. A single reagent dispensing station is provided. The cuvette and detection system are rotated as a unit to permit constant monitoring while samples are presented to the dispensing station. Further, the several samples can be tested for both prothrombin time and activated partial thromboplastin time utilizing the same light source so as to prevent any error in the readings.

By utilizing the automatic clottage detection system of the invention, there is provided a fixed time for the activated partial thromboplastin time test in that there is a fixed incubation time for these tests. Reagent is added at the dispensing station in accordance with which test is being used. Reagent is added by means of a peristaltic pump which delivers a metered amount of reagent to the desired cuvette.

Although this invention will be described with respect to its preferred embodiments, it should be understood that many variations and modifications will be obvious to those skilled in the art, and it is preferred, therefore, that the scope of the invention be limited, not by the specific disclosure herein, but only by the appended claims.

THE PREFERRED EMBODIMENTS

Figure 1:
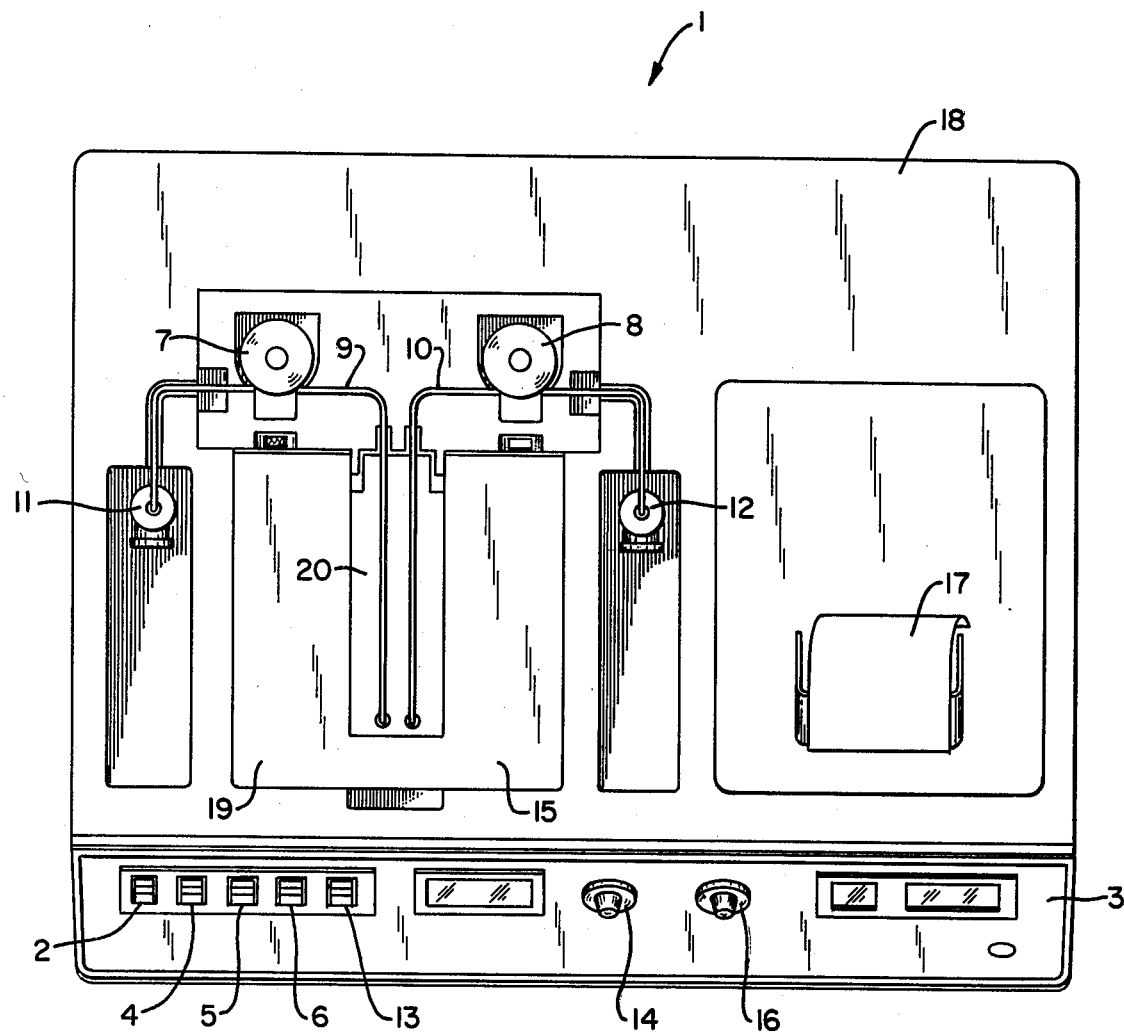
FIG. 1 is a top view of an automatic detector device incorporating the present invention.

Referring to FIG. 1, apparatus 1 of the present invention is turned on and off by switch 2 located on front panel 3. The test mode is set by switch 4, which determines whether the system operates for prothrombin time measurements, or activated partial thromboplastin time, or whether there will be a simultaneous prothrombin time (PT) and activated partial thromboplastin time (APTT) in testing of the samples.

Priming switches 5 and 6 activate peristaltic pumps 7 and 8, respectively, to fill the respective tubing 9 and 10 with reagent from the respective bottles 11 and 12. Switch 13 initiates the test cycle.

Rotary switch 14 is used to select the first sample for testing in cuvette tray 15 and rotary switch 16 is used to set the last sample to be tested. A permanent record of test results is provided on paper 17. Below cuvette tray 15 which is located in a recess in top panel 18 is rotatable detection unit 100 shown in FIG. 2.

Figure 2:
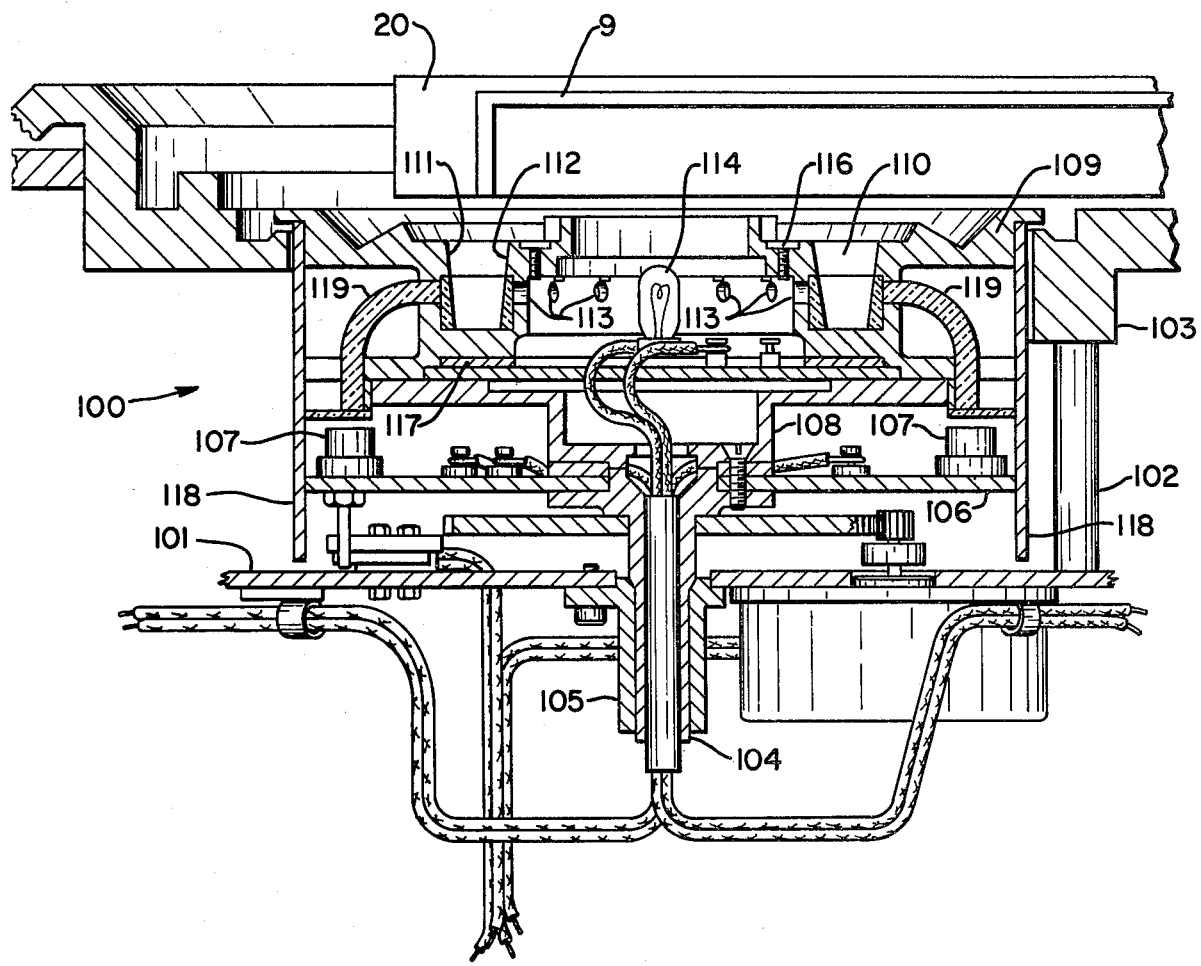
FIG. 2 is a side view in section of the rotatable detection unit of the present invention.
Figure 3:
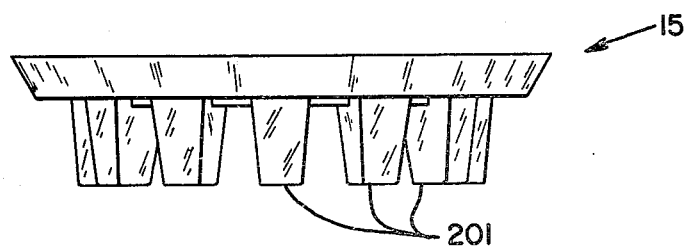
FIG. 3 is a side view of a cuvette tray suitable for use with the detection unit of the present invention.

Referring to FIG. 2, horizontal mount 101 for rotatable detection unit 100 is fastened to posts 102 (one shown) extending from instrument frame 103. Hollow shaft 104 is rotatably carried by bearing 105 which, in turn, is secured to horizontal hollow shaft 104 for rotation therewith. Twelve light detectors 107 are spaced equidistant adjacent to their periphery and facing upwardly on printed circuit board 106. Spacer 108 is secured to the top of printed circuit board 106 and supports metal receptacle 109. Receptacle 109 has an annular groove 110 in the top adapted to receive the cuvette portion 201 of cuvette tray 15 (see FIG. 3). Side walls 111 and 112 of annular groove 110 are tapered inwardly to correspond with the taper of the side walls of cuvette portion 201. Side wall 112 has twelve light passages 113 extending radially therethrough for permitting light from bulb 114 to illuminate each cuvette portion 201 of cuvette tray 15. Twelve light attenuating screws 116 are adjustable to provide uniform illumination through each light passage 113. Light transmitted through cuvette portion 201 is conducted to each of the respective light detectors 107 by light pipes 119. Heater 117 warms metal receptacle 109 to maintain test samples in cuvette portions 201 at a constant selected temperature.

Ring 118 of the detection unit, surrounds the periphery of printed circuit board 106 and metal receptacle 109 to prevent stray light from reaching light detectors 107 other than through light pipes 119.

What is claimed is:

1. A rotatable detection unit in an instrument for supporting a cuvette tray having a plurality of samples to be evaluated by the instrument, which comprises a horizontal mount carried by said instrument, a rotatable, hollow shaft extending vertically through said mount, said hollow shaft having an axis, a circular printed circuit board fixed to one end of said shaft and rotatable therewith, a plurality of light detectors spaced equidistant adjacent the periphery of said circuit board, a hollow, metal, receptacle means having an annular groove adapted to receive the cuvette portion of the tray, said annular groove being concentric to said axis, a spacer connecting said receptacle to said circuit board for rotation therewith, a light source positioned on said axis in a plane passing through said annular groove, a plurality of light passages extending radially in said plane through said receptacle to said annular groove for illuminating a respective plurality of samples, light attenuating means for providing a substantially equal amount of light exiting each of said passages, a plurality of light pipes, each of said plurality of light pipes being adapted to conduct light received from a respective sample to a respective one of said plurality of light detectors and drive means to selectively rotate said shaft.

2. The detection unit of claim 1 further including control means for sequentially positioning the plurality of samples at a reagent dispenser.

3. The rotatable detection unit according to claim 1 wherein said printed circuit board carries amplifying means for each of said detectors and multiplexing means for reducing the electrical connections to said unit.

* * * * *